United States Patent [19]

Backus et al.

[11] Patent Number: 5,195,145
[45] Date of Patent: Mar. 16, 1993

[54] APPARATUS TO RECORD EPIDERMAL TOPOGRAPHY

[75] Inventors: Alan L. Backus, Los Angeles; Ronald M. Popeil, Beverly Hills, both of Calif.

[73] Assignee: Identity Technologies Incorporated, Beverly Hills, Calif.

[21] Appl. No.: 660,967

[22] Filed: Feb. 26, 1991

Related U.S. Application Data

[63] Continuation of Ser. No. 435,186, Nov. 13, 1989, abandoned.

[51] Int. Cl.[5] .............................................. G06K 9/00
[52] U.S. Cl. ............................................ 382/4; 356/71
[58] Field of Search ..................... 382/2, 4, 5, 67; 340/825.33, 825.34; 356/71

[56] References Cited

U.S. PATENT DOCUMENTS

| | | | |
|---|---|---|---|
| 3,614,737 | 10/1971 | Sadowsky | 382/2 |
| 3,804,524 | 4/1974 | Jocoy et al. | 382/4 |
| 3,942,153 | 3/1976 | Balko et al. | 382/67 |
| 4,385,831 | 5/1983 | Ruell | 382/4 |
| 4,569,080 | 2/1986 | Schiller | 382/4 |
| 4,784,484 | 11/1988 | Jensen | 382/4 |
| 4,843,377 | 6/1989 | Fuller et al. | 382/4 |

Primary Examiner—Leo H. Boudreau
Attorney, Agent, or Firm—Keck, Mahin & Cate

[57] ABSTRACT

Apparatus and methods to accurately scan and record the skin surface topography. More particularly, the present invention has embodiments which can accurately scan fingerprints. Embodiments described each utilize a support surface penetrated by one or more openings. Skin surfaces to be scanned are rested on the supporting surface and are caused to be moved relative to the openings. Means to scan the skin surface topography as observed through the openings are located on the opposite side of the supporting surface from the skin surfaces to be scanned.

Method and apparatus are described to facilitate credit transactions.

2 Claims, 4 Drawing Sheets

APPARATUS TO RECORD EPIDERMAL TOPOGRAPHY

This application is a continuation of application Ser. No. 07/435,186 filed Nov. 13, 1989 now abandoned.

BACKGROUND

1. Field Of Invention

This invention relates to apparatus and methods to accurately scan and record skin surface topography. More particularly, the present invention has embodiments which can accurately scan fingerprints.

2. Description Of Prior Art

It has been established that fingerprints as well as other epidermal topography can be used to uniquely identify individuals. Such identification has been used for many years to help solve crimes, provide positive identification for security, identify missing persons, etc.

More recently devices have been introduced to electronically scan fingerprints and other skin surfaces. These devices typically produce signals which are inputted into computers which in turn match the signals to images stored in computer memory.

These scanning devices can generally be divided into two groups: those using optics to scan, and those using mechanical sensing means.

Most of the devices using optics have the finger tip, or other skin surface to be scanned, placed on a transparent surface. Light is shown from the underside of the transparent surface toward the finger tip or skin surface, and the reflection of the light is detected by optical sensors which output a signal containing the fingerprint or other skin surface image.

Devices using mechanical sensing means to survey finger tip, or other skin surface, have the finger tip or skin surface to be scanned placed on a sensor plate which detects minute differences in pressure caused by skin surface features.

Both of these approaches to scanning fingerprints and other skin surfaces have substantial disadvantages.

Devices using optics rely on clear and distinct images of skin surface features being displayed on the transparent surfaces on which the skin surfaces are placed. All finger tips, even freshly washed finger tips, leave residues of oil and moisture on surfaces they contact. Such residues are what allow criminologists to obtain latent fingerprints hours, days and even weeks after a criminal has touched a surface.

A fingerprint, or other skin surface, scanning device which relies on optical reflection from a transparent surface can be confused by such residues and thus such devices tend to report erroneous skin surface features after several uses. Excessively oily, dirty or moist skin also tends to make devices relying on transparent surface optics less accurate.

Devices relying on mechanical sensing means to scan finger tip or other skin surface features generally utilize matrices of delicate pressure sensing circuits. Such matrices tend to be temperamental under ideal conditions. Temperature changes, residues, moisture, and sun light exacerbate problems of accurate reporting by these devices.

OBJECTS AND ADVANTAGES

In view of the foregoing drawbacks and deficiencies of the prior art, it is an object of the present invention to provide apparatus which will accurately scan epidermal topography.

It is another object of the present invention to provide embodiments which will accurately scan fingerprints.

It is another object of the present invention to provide embodiments for uniquely identifying individuals utilizing features of their skin surface topography.

It is another object of the present invention to provide embodiments which will accurately scan epidermal topography without their accuracy being impaired by residues left from earlier epidermal contact.

It is another object of the present invention to provide embodiments which will facilitate extending credit to individuals.

Readers will find further objects and advantages of the invention from a consideration of the ensuing description and the accompanying drawings.

SUMMARY OF INVENTION

The present invention provides apparatus and methods to accurately scan epidermal topography. Embodiments of the present invention rely upon observation of a skin surface through one or more openings in a supporting surface while the skin surface is moved relative to the openings. These openings may be through holes rather than transparent light openings, and in that sense may be referenced as orifices.

Embodiments of the present invention have a guiding surface penetrated by one or more openings. Skin surfaces to be scanned are placed in contact with this guiding surface and they are moved relative to the one or more openings. During this movement, one or more scanning sensors on the opposite side of the guiding surface from the skin surface, scan successive sections of the skin surface through the openings.

Some embodiments of the present invention also employ tracking sensors to determine the amount of skin surface movement relative to the openings.

In such cases, a computer or other logical device may be used to integrate the outputs from the scanning and tracking sensors to form an image of the skin surface.

In embodiments not employing such tracking sensors, logical apparatuses are used to identify patterns on the skin surface which can uniquely identify the skin surface.

Because the skin surfaces are scanned through openings, there are no surfaces upon which residues may be deposited to obscure the device's accuracy.

Embodiments of the present invention are inherently accurate. Images observed through an opening may be recorded at any resolution, and observations of these images may be made at any intervals as the openings move relative to the skin surfaces. Thus the present invention may produce images of virtually any detail. Sensing apparatus within embodiments of the present invention may openly observe the actual skin surfaces being scanned, without being obscured by soiled transparent skin surface support platforms.

Yet the openings accurately support skin surfaces relative to the sensing apparatuses contained in embodiments of the present invention.

Embodiments of the present invention may be compact and thus may be used in locations inappropriate for more cumbersome devices. Such locations may include next to store check out stands, in automobile ignitions and locks, in door locks, etc.

Embodiments of the present invention are inherently simple and inexpensive to produce. This in turn allows their economical use in cost sensitive applications such as to verify credit card use or for home door locks.

Embodiments of the present invention may be combined with magnetic credit card readers to reduce fraud in credit transactions. Such embodiments might use two or more separate enclosures or might be combined into a single enclosure resembling one of today's stand alone credit card check stand readers with the present invention's scanner integrated on one side. Credit transactions using such embodiments would be conducted in a similar manner to today's credit transactions except purchasers using credit would be asked to have their fingerprints scanned. Information from the fingerprint scan would be stored and transmitted to credit verification companies along with other transaction information.

Embodiments of the present invention may even be used to replace plastic credit cards altogether for completing credit transactions. In such cases, a customer might go to a store check stand, identify the company with whom they have credit, give identifying information such as their name, their social security number, etc. and have their finger tip or other identifying skin surface scanned. Such transactions would have advantages over today's credit card transactions of no-card convenience for the customer, and positive identification of credit customers for the vendor and creditor.

Portable embodiments of the present invention would even allow credit and other transactions to be conveniently accomplished at restaurant tables or in the middle of store sales floors etc. information from such transactions could be immediately relayed to credit verifying computers via RF, infrared, phone lines and the like; or information could be stored for brief periods in the scanning device until the device could be connected to a phone line or other communication connection to relay the information to credit verifying computers.

DETAILED DESCRIPTION OF THE FIRST PREFERRED EMBODIMENT

Figure 1:
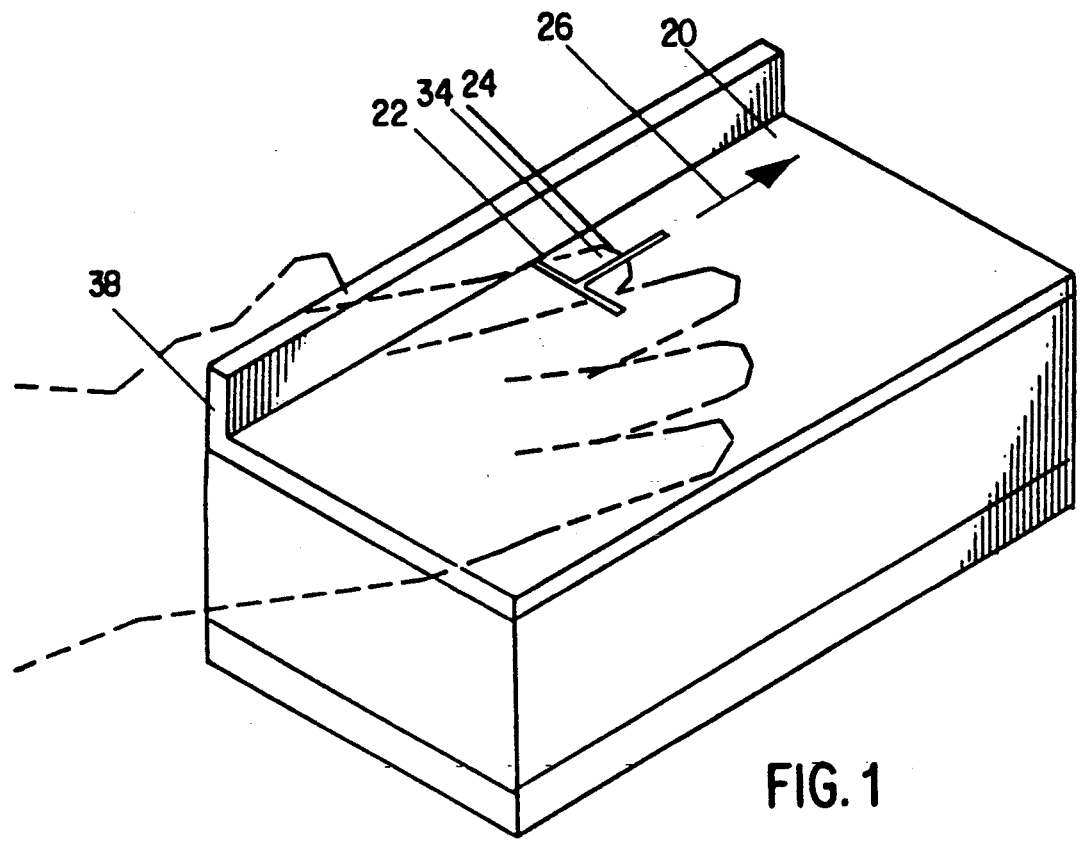
FIG. 1 is a diagrammatic representation of a scanning device constructed in accord with the present invention.
Figure 2:
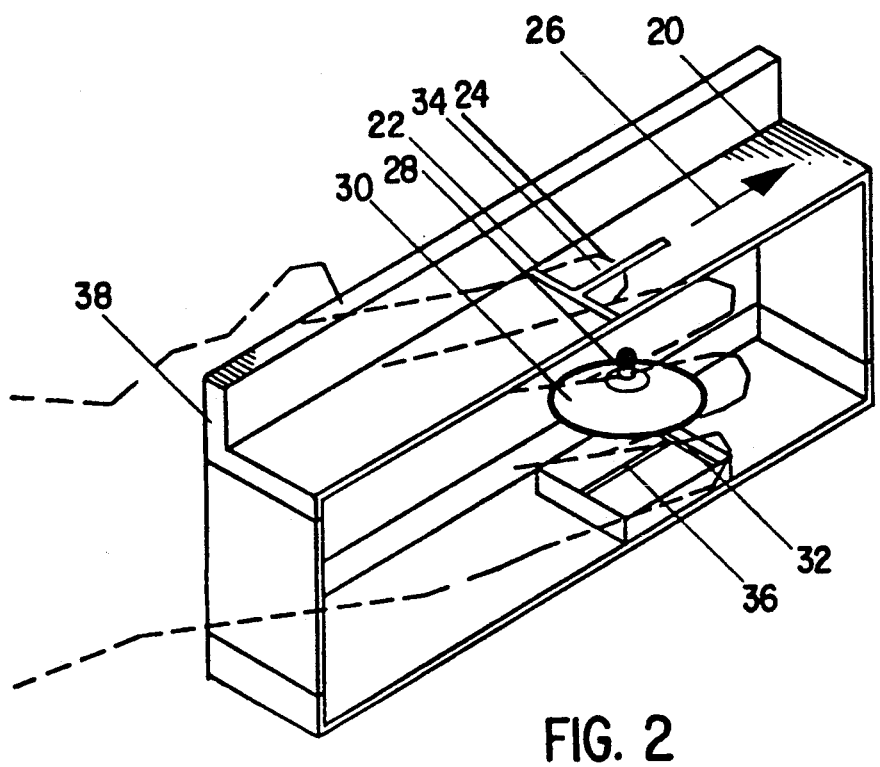
FIG. 2 shows a section taken through FIG. 1 revealing internal operating apparatus.

Referring to FIG. 1, the first embodiment of the present invention has a supporting surface 20 penetrated by a primary longitudinal slit opening 22. The supporting surface 20 supports the skin surface to be scanned while it is being scanned. FIGS. 1 and 2 show a finger tip 24 being scanned by the first preferred embodiment. The finger tip 24 is placed against the supporting surface 20 and moved linearly 26 110 in a direction essentially orthogonal to the direction of elongation of the primary longitudinal slit opening 22.

As the finger tip 24 moves over the primary longitudinal slit opening 22 successive sections of the tip's 24 surface are scanned 112 through the opening 22 by apparatus 28, 30, 32, 36 located below the supporting surface 20. Specifically, an illumination source 28 illuminates the tip's 24 surface features as displayed through the primary longitudinal slit opening 22. A focussing element 30 resolves the reflected images onto a first linear sensing array 32 which outputs signals representing linear sections of the tip's 24 surface features.

A secondary longitudinal slit opening 34, essentially orthogonal to the primary longitudinal slit opening 22, allows monitoring 114 of the finger tip's 24 movement during the scan. As the finger tip 24 moves over the secondary slit opening 34, it is illuminated by the illumination source 28. The focussing element 30 resolves the finger tip's 24 surface features onto the second linear sensing array 36 which outputs signals representing linear movement of the finger tip by tracking progress of the tip's 24 features as observed through the secondary slit opening 34. This movement sensor 28 30 34 36 tracks finger tip movement relative to the primary longitudinal slit. A guide wall 38 facilitates and controls finger tip 24 or other skin surface movement 26. Surfaces which the skin surface touches may be made of slippery material such as Delron, Nylon, Celcon or polyethylene to prevent vibration or chatter of the skin surface as the finger is moved over the slit opening. Alternatively rollers or other mechanical means might be used to reduce surface drag.

The linear sensing arrays 32 36 may be CCD or similar type sensors, or may be of other construction. Outputs from these arrays 32 36 may be thesholded to form binary signals.

The linear sensing arrays 32 36 have reciprocal geometry to the openings in the supporting surface 22 34 because of optical properties of the resolving element 30. Such lens properties are well known to those knowledgeable in the art.

Signals form the first linear sensing array 32 and the second linear sensing array 36 contain sufficient data to reconstruct the finger tip's surface topography. Such information could be digitally encoded. Methods for encoding, compressing, transmitting, reconstructing 116, and comparing these signals are well know to those knowledgeable in the art.

As an example, the two signals from the primary and secondary sensors might be combined by logical means to reconstruct an image of the finger tip's surface topography. This data then might be compressed by logical means and temporarily stored in memory. Later this information might be combined with other information, such as records of a credit card transaction, and transmitted, using modems and phone lines, to a computer or other logical device used to verify and/or record credit transactions.

Another example would use logical means to immediately compare the scanned data with scanned images stored in memory. An acceptable match might result in: a car lock or door lock opening, or a car ignition starting, or access to a secure area, etc.

A specific application for embodiments of the present invention can be found in gambling casinos. Gambling casinos have many locations under one roof where easily obtained, frequent, positive identification of individuals would be extremely useful for extending gambling credit and other purposes. Slot machines, roulette wheels, twenty-one tables, poker tables, casino restaurants, and casino shops could all be fitted with embodiments of the present invention. Wagers and/or purchases could be made with aid of fingerprint or other skin surface scan for positive verification of each transaction. Casinos could obtain at least three major benefits from this setup. First, the casino would have positive evidence that only individuals authorized to receive credit were using it. This contrasts with credit cards and personal identification numbers which can be transferred from one person to another. Second, the casino would be able to track the gambling habits of their customers to help the casino better develop their facilities. This contrasts with cash transactions where such record keeping is almost impossible. Finally, casinos could likely derive more revenue from facilities which don't have the inconvenience of using gambling chips and cash.

Another specific application for embodiments of the present invention is in recording the timely presence of individuals at specific locations. In this application an embodiment of the present invention 100 would be connected to a computer or other logical means 102 which would contain previously scanned epidermal topographical images in its memory. The logical means would have access to accurate time 104. An individual would record their presence at the location by having a section of their epidermis scanned and matched by the computer against the previously scanned images. The computer 102 would have means to record matches between the currently scanned and previously scanned images and the times when such matches occurred. Means to match digital data signal inputs with digital signals stored in computer memory are well know to those in the art, as are means to record the times when such matches occur. Such a device could provide positive proof of an individual's presence at a location at a given time.

DETAILED DESCRIPTION OF THE SECOND PREFERRED EMBODIMENT

Figure 3:
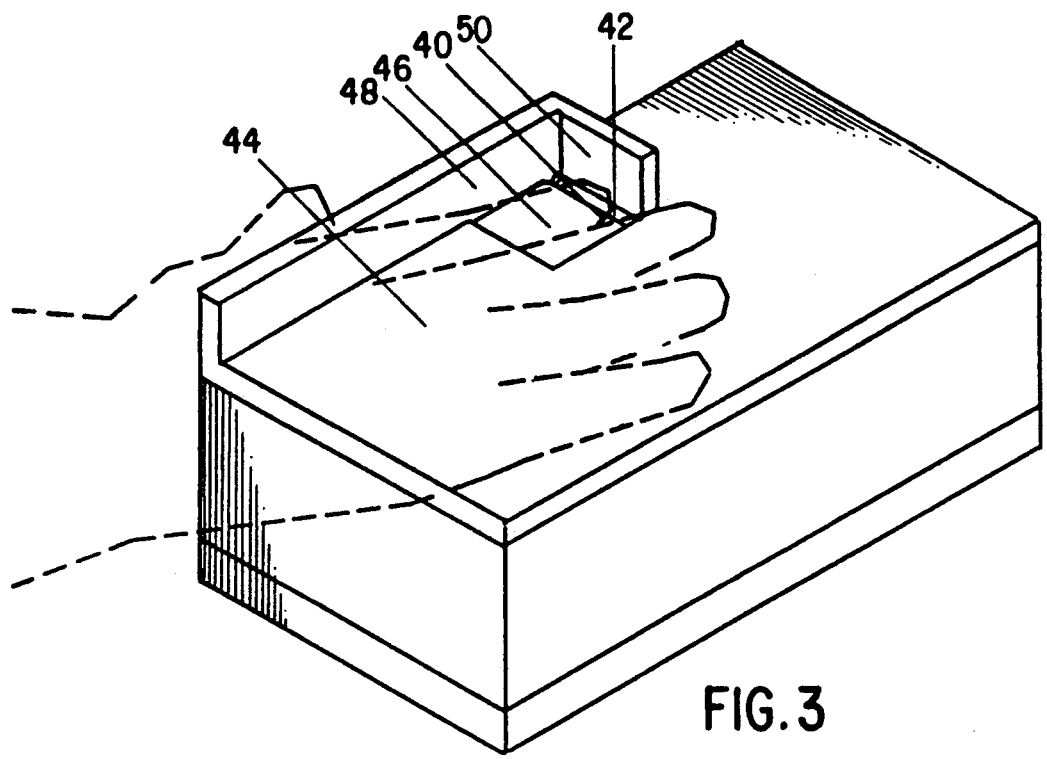
FIG. 3 is a diagrammatic representation of a second scanning device constructed in accord with the present invention.
Figure 4:
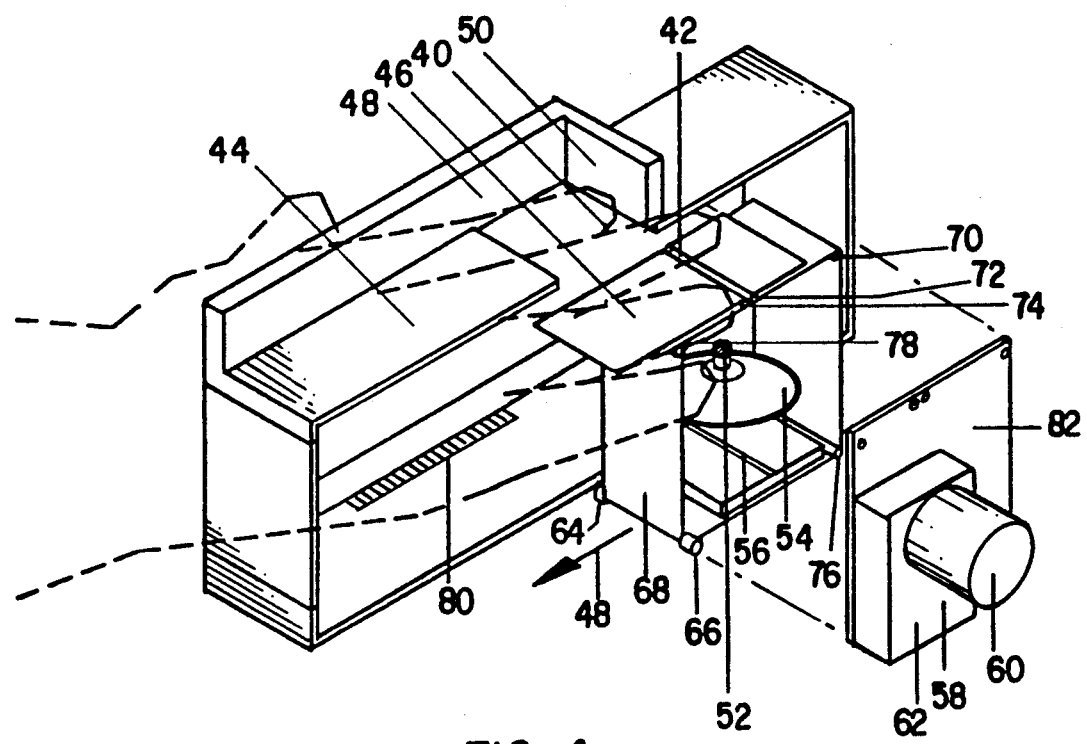
FIG. 4 shows an exploded section taken through FIG. 3 revealing internal operating apparatus.

Referring to FIGS. 3 and 4, a second scanner constructed in accord with the present invention holds the observed skin surface 40 stationary while the longitudinal slit opening 42 penetrating the supporting surface 44 46 is moved 48.

The observed skin surface, such as the finger tip 40 indicated, is positioned by a supporting surface having both rigid 44 and flexible 46 elements. Guides 48 50 position the finger tip 40 or other observed skin surface on the supporting surface 44 46. Below the supporting surface 44 46 are sensing 52 54 56 58 and drive 60 62 64 66 68 70 72 74 76 78 apparatuses mounted onto a module 82 which moves 48 relative to the finger tip 40.

Upon actuation, the module 82, propelled by a motor 60 driving gear reduced 62 pinion gears 64 66 which engage linear rack gears 80, moves 48 causing the opening 42 and all sensing 52 54 56 58 apparatus mounted to the module 82 to move 48 relative to the finger tip 40.

Figure 5:
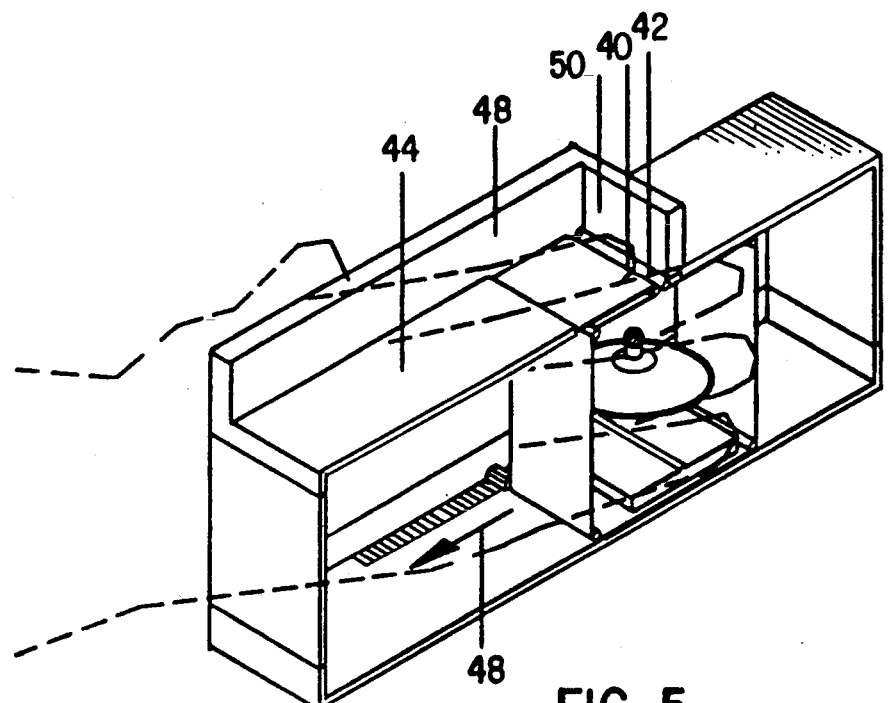
FIG. 5 shows a section taken through FIG. 3 revealing internal operating apparatus before a scan occurs.
Figure 6:
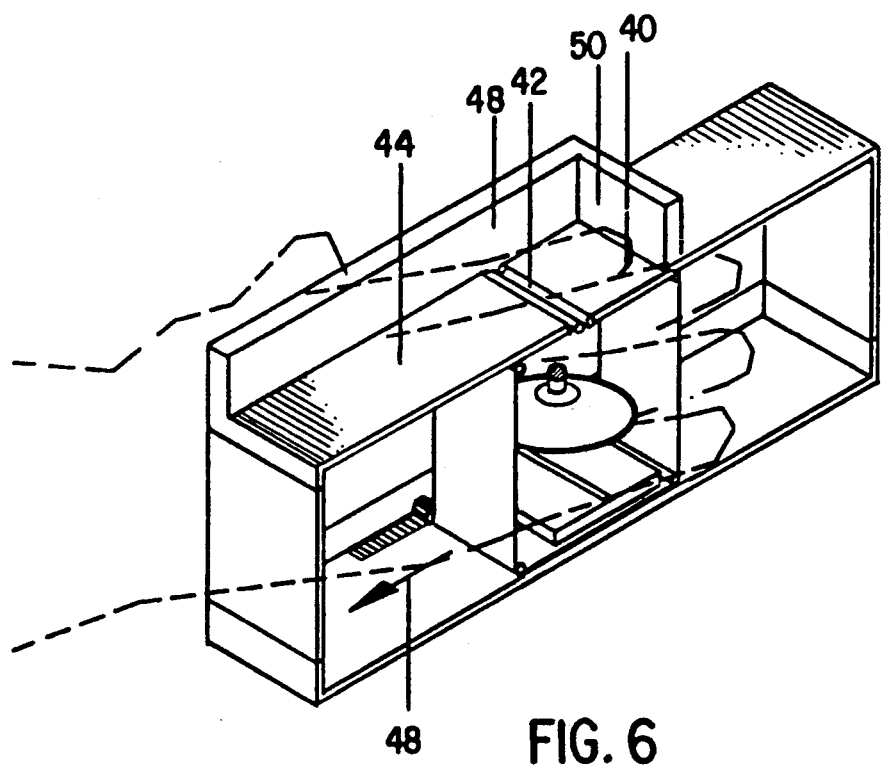
FIG. 6 shows a section taken through FIG. 3 revealing internal operating apparatus after a scan occurs.
Figure 7:
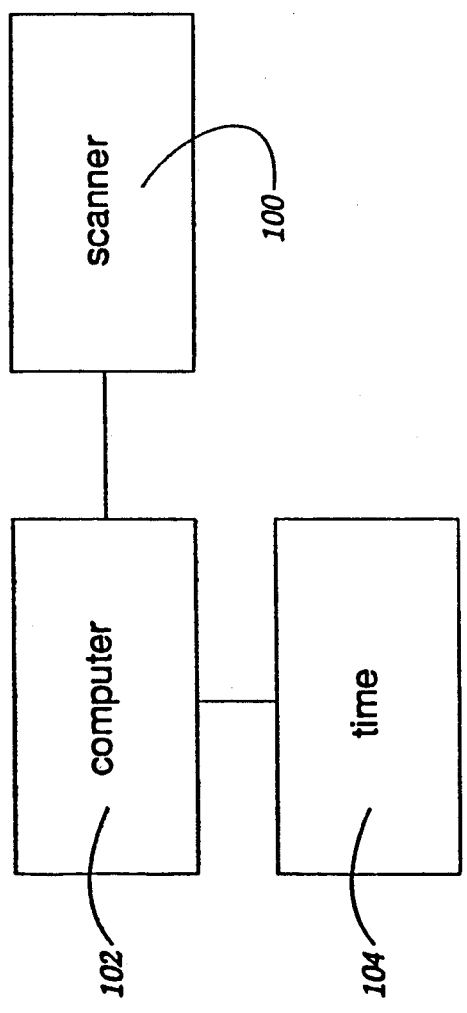
FIG. 7 shows a block diagram of a time clock device constructed in accord with the present invention.
Figure 8:
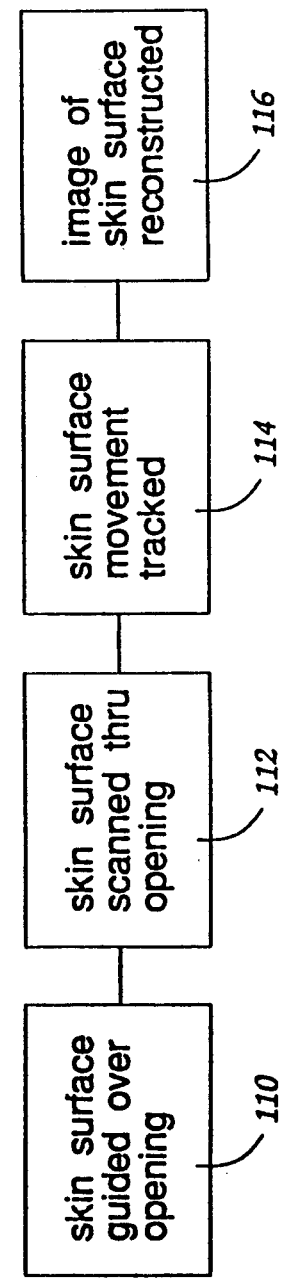
FIG. 8 shows a block flow diagram of the steps of a method for scanning a fingerprint in accord with the present invention.

FIG. 5 shows the module before this movement 48, and FIG. 6 shows the module after. During the movement 48, the opening 42 which is created by a flexible ribbon 68 tensioned by rollers 72 74 mounted to the module 82, moves the length of the observed skin surface 40.

Sensing apparatus 52 54 56 58 also mounted to the module 82, moves with the longitudinal slit opening 42 and observes the skin surface 40 at regular intervals through the longitudinal slit opening 42. This sensing apparatus includes: illuminating means 52 which illuminates the observed skin surface 40, resolving means 54 to focus the skin surface's image, and first sensing means 56 to detect the focused image.

Second sensing means 58 within the gear housing 62 monitors the module's 82 linear movement 48.

A computer or other logical device may be used to combine the outputs from the first 56 and second 58 sensing means to create an image of the observed skin surface 40.

The flexible 46 supporting surface is maintained during module 82 movement 48 by the flexible ribbon 68 which creates it being wrapped around the module's periphery by supporting rollers 70 72 74 76 78. As the module moves 48, these rollers 70 72 74 76 78 allow ribbon movement from one side of the longitudinal slit opening 42 to the other by way of movement around the module's 82 periphery.

At the end of each scan, the motor 60 is reversed and the slit is reset to its initial position.

Both the first and the second preferred embodiments may require light blocking hoods over their openings to prevent ambient light from striking the sensing means.

Both the first and second preferred embodiments may not need secondary sensors to detect movement of a skin surface relative to their primary slit openings. Instead, logical means observing images appearing in the slit openings could create a pseudo images of skin surfaces based on the geometry of the skin surface patterns. As an example, a logical device could record a slit image every time it observed a skin surface ridge which was parallel with slit opening. The composite of such recorded images might not physically resemble the actual skin surface, but it could still uniquely identify the skin surface.

Either the first or the second preferred embodiment could use secondary sensors to verify that the topography being observed is that belonging to skin. As an example sensors placed in proximity to the opening or openings could sense galvanic skin response which wouldn't be present in plastics which might be used to feign fingerprints or other skin surfaces.

Either the first or the second preferred embodiment could be contained in a single portable enclosure. Logical means to process sensor thresholded binary signals are very compact as can be readily seen from today's portable computers. Means to wirelessly relay such signals using RF or light are also well known and very compact. And all the above mechanisms are able to be operated by battery.

Such a portable units could even have keypads to enter data as well as have magnetic strip readers or other scanners to directly enter credit card data. Such portable devices could facilitate conducting credit transactions in locations ranging from sales floors to restaurant tables. information could be relayed in real time to credit transacting facilities via RF, light and phone lines or the like, or it could be temporarily stored until the unit could be brought to a location where its information could be downloaded to such facilities via phone lines or other communication means.

Methods for matching digital signals in general, and fingerprints and other epidermal topography in specific are well known to those knowledgeable in the art, and are extensively represented in issued U.S. patents.

Logical devices capable of executing algorithms to match epidermal surface features are also known to those knowledgeable in the art and are widely available. These devices include, but are not limited to: personal, mini, and mainframe computers.

Activation means for the disclosed embodiments may include, but are not limited to: instructions to users; motors and other embodiment drive mechanisms; switches; software used by logical devices; etc.

Relative movement between epidermis being scanned and opening or openings in supporting surfaces may be caused by: movement of the epidermis, movement of the opening or openings, or some combination of both.

What have been described are certain aspects of apparatus to scan skin surface topography. It is understood that the foregoing descriptions and accompanying illustrations are merely exemplary and are in no way intended to limit the scope of the invention, which is defined solely by the appended claims and their equivalents. Various changes and modifications to the preferred embodiments will be apparent to those skilled in the art. Such changes and modifications may include, but are not limited to: sensing means other than optics, such as sonar or holographic interference or capacitance or inductance etc., being used to scan skin surfaces through the opening or openings; tracking sensors other than reflective optics, such as one or more rollers which contact the skin surfaces while their topography is being scanned or breaking light beams or pressure sensitive surfaces or plungers or pivoting rods or galvanic resistance sensors or capacitance sensors or inductance sensors, being used to track linear skin surface movement relative to the opening or openings; moving the opening or openings while leaving the skin surface stationary; scanning skin surfaces in different axes such as from side to side or up and down or diagonally; modifying the shape of the opening or openings so they are curved or non-linear; changing the shape of the supporting surface so it's not flat by making it a simple or compound curve or having other configurations which might be adaptable to supporting skin surfaces; changing the scale of the device so it might scan several fingers or entire hands or feet or other skin sections; changing the shape of the opening or openings penetrating the supporting surface to round, rectangular, or other shapes; the opening or openings occurring at the edge of the supporting surface so the skin surface is scanned as it passes over the edge; having a minimal supporting surface such as the edges of two walls with the opening or openings occurring between the wall edges; using more than one opening to scan the skin surface, with such openings being parallel or intersecting or independently positioned relative to one another; using a wide opening or openings through which both skin surface topography and skin movement is sensed; placing illumination and focussing means in configurations or locations other than those indicated such as linear arrays of illumination elements or smaller focussing elements surrounded by illumination elements; etc.

Such changes and modifications can be made without departing from the spirit and scope of the invention. Accordingly it is intended that all such changes and modifications be covered by the appended claims and equivalents.

We claim:

1. Apparatus for surveying skin surface features, comprising:
    a first surface penetrated by a first orifice,
    means to facilitate and control movement on said first surface of skin surfaces across said first orifice,
    said means to facilitate and control movement comprising a straight linear guide disposed above and traversing said first surface,
    a first sensor surveying skin surface features through said first orifice,
    a second sensor tracking skin surface movement relative to said first orifice,
    whereby a representation of two dimensional skin surfaces is composed by combining signals from said first sensor and said second sensor.

2. The apparatus of claim 1 wherein said first orifice is a straight slit and said straight linear guide comprises a straight linear flat wall protruding from and substantially orthogonal to said first surface, and said straight liner guide facilitates and controls skin surface movement substantially orthogonal to said straight slit.

* * * * *